(12) United States Patent
Zenanko et al.

(10) Patent No.: US 12,721,683 B2
(45) Date of Patent: Sep. 1, 2026

(54) ROBOTIC NAVIGATION AND GUIDANCE SYSTEM FOR IMPLANTING A NEUROMODULATION DEVICE

(71) Applicant: SynerFuse, Inc., Eden Prairie, MN (US)

(72) Inventors: Justin D. Zenanko, Minneapolis, MN (US); Christopher G. Frank, New Brighton, MN (US); Gregory F. Molnar, Blaine, MN (US)

(73) Assignee: SynerFuse, Inc., Eden Prairie, MN (US)

( * ) Notice: Subject to any disclaimer, the term of this patent is extended or adjusted under 35 U.S.C. 154(b) by 661 days.

(21) Appl. No.: 17/812,600

(22) Filed: Jul. 14, 2022

(65) Prior Publication Data

US 2023/0018739 A1 Jan. 19, 2023

Related U.S. Application Data

(60) Provisional application No. 63/222,637, filed on Jul. 16, 2021.

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/30* (2016.02); *A61N 1/0551* (2013.01); (Continued)

(58) Field of Classification Search
CPC ...... A61B 34/20; A61B 34/30; A61N 1/0551; A61N 1/36062; A61N 1/372; G16H 20/40; G16H 40/63
See application file for complete search history.

(56) References Cited

U.S. PATENT DOCUMENTS

| | | | |
|---|---|---|---|
| 7,515,964 | B1 | 4/2009 | Alexander |
| 10,117,580 | B1 | 11/2018 | Puryear et al. |

(Continued)

FOREIGN PATENT DOCUMENTS

| | | |
|---|---|---|
| JP | 2004-516855 | 6/2004 |
| JP | 2007-501674 | 2/2007 |

(Continued)

OTHER PUBLICATIONS

Notification Concerning Transmittal of International Preliminary Report on Patentability and International Preliminary Report on Patentability issued in PCT/US2023/065186, mailed Oct. 10, 2024.

(Continued)

*Primary Examiner* — Erin Mcgrath

(74) *Attorney, Agent, or Firm* — Barnes & Thornburg LLP; Jeffrey R. Stone

(57) ABSTRACT

The present invention provides a robotic navigation system for identifying a target nerve for guiding and/or performing the implanting a neuromodulation device at the target nerve wherein the neuromodulation device includes a pulse generator and at least one lead in electrical or operative connection with the pulse generator. In some embodiments, the location of the robotically advanced lead and electrode may be imaged and displayed on a display and/or may be visually annunciated using one or more lights to indicate whether the placement location of the lead or electrode is within or outside of a predetermined distance of the target nerve.

8 Claims, 3 Drawing Sheets

(51) Int. Cl.

| | |
|---|---|
| ***A61N 1/05*** | (2006.01) |
| ***A61N 1/36*** | (2006.01) |
| ***A61N 1/372*** | (2006.01) |
| ***G16H 20/40*** | (2018.01) |
| ***G16H 40/63*** | (2018.01) |
| *A61B 90/00* | (2016.01) |

(52) U.S. Cl.

CPC ......... *A61N 1/36062* (2017.08); *A61N 1/372* (2013.01); *G16H 20/40* (2018.01); *G16H 40/63* (2018.01); *A61B 2034/2051* (2016.02); *A61B 2034/2055* (2016.02); *A61B 2034/2065* (2016.02); *A61B 2090/363* (2016.02); *A61B 2090/373* (2016.02)

(56) References Cited

U.S. PATENT DOCUMENTS

| | | | | |
|---|---|---|---|---|
| 10,675,458 | B2 | 6/2020 | Molnar et al. | |
| 11,224,740 | B2 | 1/2022 | Sorensen et al. | |
| 11,247,046 | B2 | 2/2022 | Molnar et al. | |
| 11,471,673 | B2 | 10/2022 | Molnar et al. | |
| 11,638,817 | B2 | 5/2023 | Molnar et al. | |
| 2002/0107573 | A1* | 8/2002 | Steinberg | A61F 2/441 623/17.12 |
| 2005/0055065 | A1 | 3/2005 | Campbell | |
| 2006/0089640 | A1 | 4/2006 | Bleich et al. | |
| 2008/0150169 | A1 | 6/2008 | Imran | |
| 2009/0054951 | A1 | 2/2009 | Leuthardt et al. | |
| 2009/0112282 | A1 | 4/2009 | Kast et al. | |
| 2010/0137938 | A1 | 6/2010 | Kishawi et al. | |
| 2011/0184308 | A1* | 7/2011 | Kaula | A61B 18/00 600/546 |
| 2011/0224682 | A1 | 9/2011 | Westlund et al. | |
| 2012/0083709 | A1 | 4/2012 | Parker et al. | |
| 2012/0277839 | A1 | 11/2012 | Kramer et al. | |
| 2012/0309237 | A1 | 12/2012 | Marzano et al. | |
| 2013/0310901 | A1 | 11/2013 | Perryman et al. | |
| 2015/0165193 | A1 | 6/2015 | Imran | |
| 2016/0213917 | A1 | 7/2016 | Dalm et al. | |
| 2016/0339251 | A1 | 11/2016 | Kent et al. | |
| 2017/0001003 | A1 | 1/2017 | Pivonka et al. | |
| 2017/0071682 | A1 | 3/2017 | Bar et al. | |
| 2017/0095667 | A1 | 4/2017 | Yakovlev et al. | |
| 2017/0196508 | A1 | 7/2017 | Hunter | |
| 2017/0312499 | A1 | 11/2017 | Linker et al. | |
| 2017/0348061 | A1 | 12/2017 | Joshi et al. | |
| 2018/0192943 | A1 | 7/2018 | Annoni et al. | |
| 2018/0317771 | A1 | 11/2018 | Puryear et al. | |
| 2018/0318579 | A1 | 11/2018 | Puryear et al. | |
| 2018/0325610 | A1* | 11/2018 | Cameron | G06T 7/74 |
| 2019/0008386 | A1 | 1/2019 | Puryear et al. | |
| 2019/0009083 | A1 | 1/2019 | Webster et al. | |
| 2019/0192874 | A1 | 6/2019 | Shukla | |
| 2019/0380789 | A1* | 12/2019 | Link | A61B 34/20 |
| 2020/0030601 | A1 | 1/2020 | Molnar et al. | |
| 2020/0108252 | A1 | 4/2020 | Zellmer et al. | |
| 2020/0222692 | A1 | 7/2020 | Molnar et al. | |
| 2021/0001114 | A1 | 1/2021 | Wolf, II | |
| 2021/0030488 | A1 | 2/2021 | Sachs | |
| 2021/0178168 | A1 | 6/2021 | Janzig et al. | |
| 2021/0275823 | A1 | 9/2021 | Sell | |

FOREIGN PATENT DOCUMENTS

| | | |
|---|---|---|
| JP | 2012-506759 | 3/2012 |
| JP | 2012-515060 | 7/2012 |
| JP | 2017 507751 | 3/2017 |
| WO | 01/60234 | 8/2001 |
| WO | 2010/062622 | 6/2010 |
| WO | 2010/83308 | 7/2010 |
| WO | 2018/208617 | 11/2018 |
| WO | 2021/077081 A1 | 4/2021 |

OTHER PUBLICATIONS

International Preliminary Report on Patentability issued in application No. PCT/US2022/073765, mailes Jan. 25, 2024.

International Search Report and Written Opinion dated Dec. 7, 2023, prepared in International Application No. PCT/US2023/065186.

International Search Report and Written Opinion issued in PCT/US2022/73765, mailed Nov. 21, 2022.

International Search Report and Written Opinion issued in PCT/US2022/75720, mailed Nov. 23, 2022.

International Preliminary Report on Patentability issued in PCT/US2019/43138, dated Jan. 26, 2021.

Extended European Search Report, dated Apr. 13, 2022 for European Patent Application No. EP19840582.1 based on PCT Application No. PCT/US2019/043138.

International Search Report and Written Opinion issued in PCT application No. PCT/US2019/43138, mailed Oct. 15, 2019.

Extended European Search Report issued in EP 19808957, dated Feb. 16, 2021.

International Preliminary Report on Patentability issued in PCT/US2019/043136, dated Jan. 26, 2021.

* cited by examiner

ROBOTIC NAVIGATION AND GUIDANCE SYSTEM FOR IMPLANTING A NEUROMODULATION DEVICE

CROSS-REFERENCE TO RELATED APPLICATIONS

This application claims the benefit of provisional application 63/222,637, filed Jul. 16, 2022 and entitled ROBOTIC NAVIGATION AND GUIDANCE SYSTEM FOR IMPLANTING A NEUROMODULATION DEVICE the contents of which are hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to a system and/or method for the treatment of chronic spinal pain comprising a robotic navigation and guidance system in combination with implantation of a neuromodulation device.

Description of the Related Art

Neuromodulation for the treatment of chronic spinal pain is a procedure that has been in use for decades. The procedure is generally prescribed to a patient only after they have gone through a spinal procedure that may involve vertebral fusion in an effort to mitigate and/or correct the supposed source of the pain. However, often such spinal procedures do not resolve the pain issues. After weeks, months and perhaps years of continued chronic pain and pain therapy through medications, including opioids, the patient may finally be prescribed neuromodulation for the treatment of chronic pain after failed back surgery.

The art does not provide single-surgical-procedure solutions that address these issues.

Further, advances in robotics and navigation have resulted in robotic surgical navigation and guidance systems for use in the performance of spinal fusion procedures. Such robotic systems include the Mazor X Stealth Edition™ robotic guidance system for spinal surgery provided from Medtronic, and the ExcelsiusGPS® robotic navigation platform from Globus Medical. These robotic and navigation systems, however, only relate to the performance of a spinal procedure and not to placement of the neuromodulation device.

Accordingly, it would be highly advantageous to provide a surgical method and system that enables both a spinal procedure and neuromodulation system implantation within a single procedure.

It would be further highly advantageous to provide robotic navigation and guidance for placement of the surgical fusion device and the neuromodulation device.

It would be a further advantage to provide robotic navigation and guidance for placement the neuromodulation system in cases where a spinal fusion device is not prescribed or is performed as a separate procedure.

Various embodiments of the present invention address these, inter alia, issues.

The figures and the detailed description which follow more particularly exemplify these and other embodiments of the invention.

DETAILED DESCRIPTION OF THE INVENTION

Figure 1:
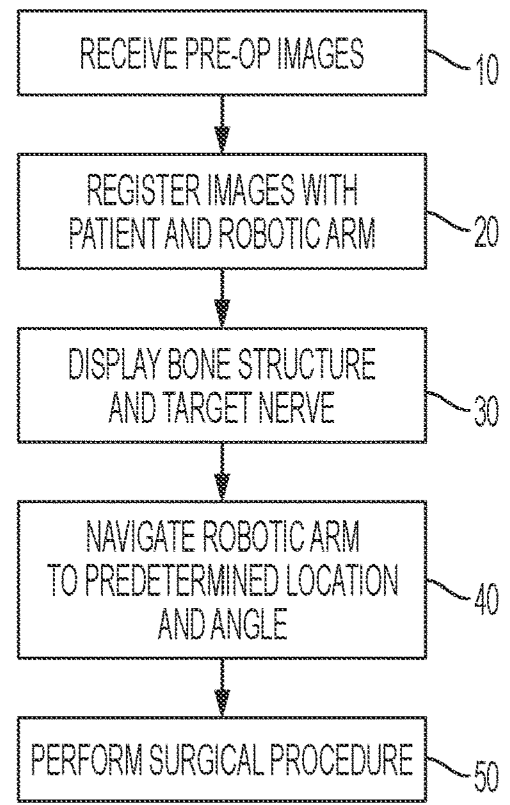
FIG. 1 is an exemplary process diagram of a one embodiment of the present invention.

Generally, various embodiments of the present invention are based upon the premise that many patients who suffer from chronic back pain, such as those who suffer for a long enough period of time or due to the severity of their particular condition, are also separately suffering from neuropathic pain that cannot be corrected by spinal surgery. In such a case it is a misnomer to say that a patient is suffering from "failed back surgery" but more accurately that the back surgery simply does not address the neuropathic pain that may have been in place prior to the back surgery.

The present invention provides a method for combining the implantation of a spinal treatment device with the implantation of a neuromodulation device, or at least a neuromodulation lead of a neuromodulation device, into a single combination procedure performed at the spinal treatment site. The present invention thus provides the potential to treat both back stabilization issues and neuropathic pain issues in a single procedure, with the additional benefit of minimizing the amount of pain medications, including opioids and other pain medications that a patient may otherwise require to manage chronic back pain.

Robotic surgical navigation systems are known in the art. Exemplary known robotic system include a workstation and a guidance system. The workstation may include a touch screen panel and a control system, which is the hardware that controls the robotic system and the guided system. The guidance system includes a table mounted robotic arm. Also included in the prior art system is a control panel and a navigation camera and a suite of navigation instruments for use with the robotic arm and robotic surgical system.

Use of the known robotic surgical systems includes a surgical planning step. A surgery may be planned prior to the actual surgical procedure beginning by performing a preoperational CT scan. Alternatively, a surgical plan may be performed during the surgery using an O-arm to scan the patient. In either case, the scan captures an anatomical area of interest, which in the prior art is generally limited to the spine and the bony structures such as the vertebrae, such as in the use case of a spinal fixation procedure. The scan may capture each vertebrae of the region of interest and the vertebrae are segmented via an anatomical landmark recognition algorithm using fiducial markers, identified or placed during the scan, in order to map a three-dimensional location of the patient spinal structure relative to the robotic navigation system.

The next step in the surgical planning phase using a known robotic surgical system is to determine the ideal orientation of each vertebrae and from that idea orientation to plan where the implants will be added. Surgical planning occurs by reviewing the scanned images on a display and then being able to view a virtual implant such as a rod or screw on the display in order to visualize how the implant can be optimally placed in the bone structure.

An exemplary planned surgical implant may provide for a set of pedicle screws to be inserted into the vertebrae that is targeted; a well-known stabilization system. The angle of entry of the screws can be adjusted during the planning procedure as can the location of entry of the screws into the target bony structure. The display has a navigation element that allows for scrolling and rotation and viewing of different slices of the scan along a two-dimensional plane. The process described with respect to a first and second set of screws or particles can be repeated at additional spinal levels as required by the planning process in order to treat the patient.

Upon completion of the surgical planning step, surgical preparation is performed in order to utilize known robotic navigation system. A rigid bed is used in combination with patient fixation in order to ensure robotic precision. The 3D camera maps the surface of the operating field and patient registration via fiducial's, this step is performed with a mapping of the pre-operative images and planning information to a CT and fluoroscopic scan of the patient. Each vertebral body of the patient is registered independently using a segmental merge so that the anatomy of the region of interest of the patient, such as the vertebrae and or other spinal and bony structures, are mapped to the images from the surgical plan.

Still referring to known robotic navigation systems and use thereof, a rigid bed may be used in combination with patient fixation in order to ensure robotic precision. The 3D camera maps the surface of the operating field and patient registration via fiducial's, this step is performed with a mapping of the pre-operative images and planning information to a CT and fluoroscopic scan of the patient.

Each vertebral body of the patient is registered independently using a segmental merge so that the anatomy of the region of interest of the patient, such as the vertebrae and or other spinal and bony structures, are mapped to the images from the surgical plan for use with the known robotic navigation systems.

Once the surgical preparation step has been completed, the surgical performance may be performed. Navigation with known robotic navigation systems occurs via the integrated camera with spatial tracking, allowing for display of the position of the robotic arm with respect to the patient anatomy and bony structures of the patient's anatomy, any of which may additionally be displayed on the display.

A registration template may be used to enable the navigation capabilities of the known robotic navigation systems, ensuring accurate movement of the robotic arm in the three dimensional plane with respect to the patient's anatomy.

Once registered, the robotic arm moves according to a preplanned trajectory and the instrumentation is used through the robotic arm, such instrumentation being guided by the robotic arm to a predetermined surgical location and at a predetermined angle of entry in three-dimensional space.

While the surgical performance step is being performed, the known robotic navigation system may allow for real-time visualization of the surgical procedure on the display, including showing the patient anatomy, bone structure, along with the current and target location of the surgical pedicle screws including the relation between the surgical pedicle screws, angle of entry and location of entry with respect to the target vertebrae or bony structure.

Figure 2:
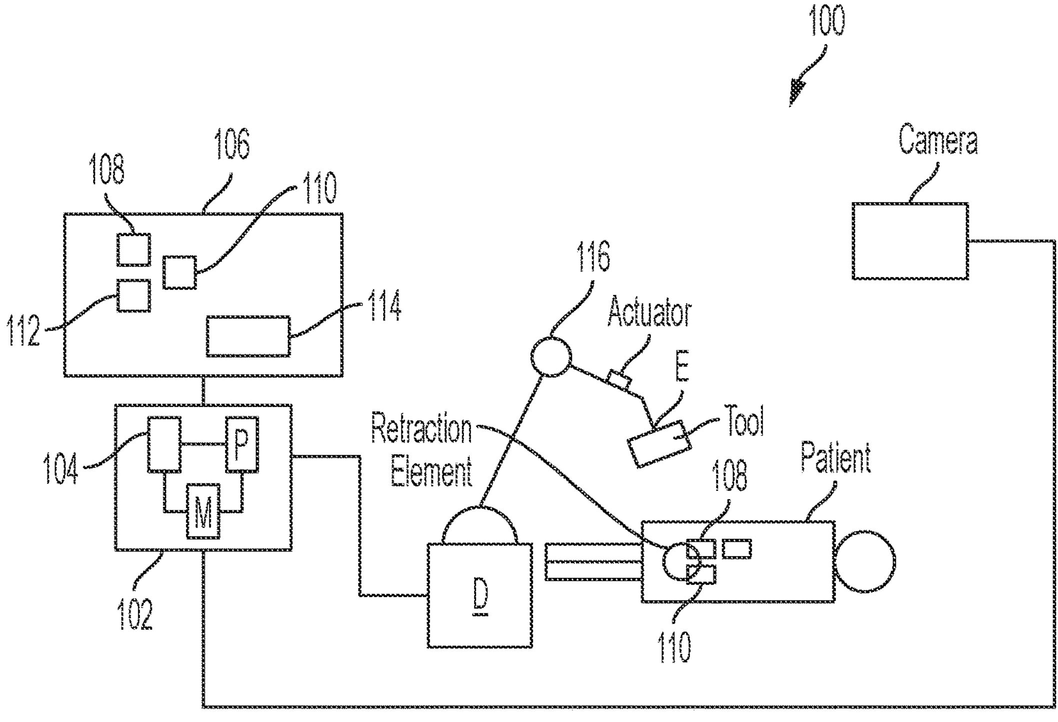
FIG. 2 illustrates one embodiment of the present invention.

Turning now to FIGS. 1 and 2 an embodiment of a flow or process chart of a procedure using one embodiment of the present invention and an exemplary diagram of one embodiment of an exemplary robotic navigation system in use. Such robotic navigation system may be used for, among other things, identifying a target nerve for implanting a neuromodulation device either alone, or in combination with a spinal procedure as discussed above.

Figure 4:
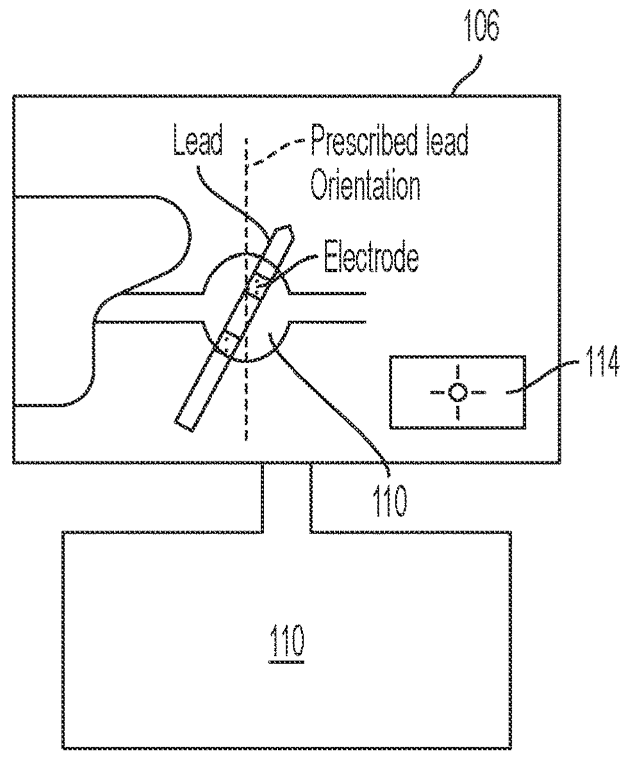
FIG. 4 illustrates one embodiment of the present invention.

FIG. 1 begins by taking pre-op images of the operative area, with reception of same into the robotic navigation system in step 10, followed by registration of the images with the system, patient and robotic arm in step 20. The imaged related bone structure of the operative area and an imaged target nerve are displayed by the system in step 30. Step 40 comprises navigation of the robotic arm of the robotic navigation system to a predetermined location and angle. Finally, step 50 comprises the performance of the surgical procedure itself. In addition, and as shown in FIG. 4, a lead and/or electrode(s) thereon may be oriented over or next to a target nerve according to a predetermined orientation for that target nerve.

Turning now to FIG. 2, the exemplary robotic navigation system 100 comprises a control system 102 for receiving three-dimensional preoperative data, e.g., images. The preoperative data may include, but is not limited to information, regarding the spatial location of the bone structures of two adjacent vertebrae, such as for performing a spinal fixation procedure.

The robotic navigation system 100 further includes a registration system 104 within its control system that allows the relationship between a coordinate system of the surgical robotic arm, in combination with the control system 102, to map to the three-dimensional preoperative data. As is known in the art, the control system 102 may comprise a processor P with preprogrammed instructions, a memory M in operative communication and connection with the processor P, wherein the processor P is configured to execute the preprogrammed instructions and communicate with a display to which the processor P and/or control system 102 is in operative communication and connection. The incision location, incision depth, angle of entry, location of target and/or predetermined orientation of lead(s) and/or electrode(s) may all be predetermined and may be stored within processor P and/or memory M for execution of programmed instructions by processor P directing the robotic arm 116 to execute the procedure(s).

Thus, the robotic navigation system 100 further includes a display 106 for displaying the bone structures 108 and the target nerve 110 and other anatomical markers of interest 112 in the surgical region of interests. The control system, or the processor of the control system executes the preprogrammed instructions, may calculate an estimated target nerve location 114 based upon the three-dimensional preoperative data. The control system 102 may communicate to the display 106 a virtual indicator 114 of the target nerve location on the display screen in the estimated target nerve location relative to the bone structures.

The target nerve may include the spinal cord or the dorsal root or the dorsal root ganglion or any more narrow regions of a target nerve, such as (1) a specific area of the spinal cord, or (2) level of the spinal cord, or (3) a specific area or angle, or (4) zone of entry or orientation with respect to the dorsal root ganglia or other such target nerves. In one embodiment, the target nerve can be estimated based upon an MRI of the patient during a surgical planning step. In such case, the target nerve is identified from the MRI image itself. In another embodiment the estimated target nerve location can be based upon an estimated anatomical distance from a bone structure or one or more bone structures or sub elements of both structures and/or other anatomical features obtained in a pre-operative scan.

In another embodiment the estimated target nerve location can be determined using machine learning by providing the estimated target nerve location based upon an annotated screening set of multiple bone structure images and corresponding target nerve locations. In yet another embodiment the target nerve location can be identified based upon and evoked response.

FIG. 2 further illustrates a robotic navigation system 100 for accessing a target nerve 110 during a spinal procedure. Robotic navigation system 100 includes control system 102 as described above, configured for receiving three-dimensional preoperative data including information relating to the spatial location of bone structures 108 of two adjacent vertebrae. The robotic system 100 further includes a registration system 104, also as discussed above, and configured to relate the coordinate system of the surgical robotic arm 116 and as provided in the programmed instructions of control system 102 with the three-dimensional preoperative data. The robotic navigation system 100 thus further includes a robotic arm 116 with associated, as known in the art, drive mechanism D configured to move the robotic arm 116, and at least an end effector E configured for grasping and/or manipulating tools and/or tissue. The robotic arm 116 is in operative communication and connection with the control system 102 and in operative communication and connection with, and configured for receiving instructions from, the control system 102 based upon a preoperative plan.

During a surgical procedure, the robotic arm 116 is positioned, via instructions from the control system 102, over a predetermined incision location of a patient's anatomy with a predetermined angle of entry based upon a preoperative planning step. The position and angle of the robotic arm 116 provides surgical navigation via the end effector E and associated tool or device held or otherwise disposed therein or thereon, and access to the target nerve based upon location and also angle of entry.

The robotic navigation system 100 may include a robotic arm 116, or more than one robotic arm 116 in communication with and operably controllable by the control system 102, each robotic arm 116 having any number of interchangeable robotic arm elements, e.g., end effectors E, that allow for surgical navigation and performance of the surgery or tools for enabling and assisting in the performance of the surgery.

In one embodiment the robotic arm 116 may comprise a cannula for guiding the incision at the predetermined location and at the predetermined three-dimensional angle of entry to the patient anatomy. In another embodiment the robotic arm includes an incision tool at effector end E for making the incision as described above.

The incision as operated or guided by the robotic arm 116 further allows for the creation of an incision at a predetermined depth and predetermined location. In one embodiment, the incision provides direct physical access to the target nerve as determined as part of the preoperative planning step. In another embodiment, after incision the target nerve is identifiable under direct visual access as a result of the predetermined incision. In another embodiment, after incision a camera may comprise the end effector E or may otherwise be connected with the robotic arm 116 and in operative connection and communication with the control system 102 and/or the display 106 in order to provide a visual display of the target nerve on the display 106. The display 106 may provide a visual indicator of the placement location of an exemplary guidance tool and/or the surgical tool currently being utilized by the robotic arm 116 and/or end effector E, with respect to the target nerve 110 and or the bony structures 108 of the area of interest.

As further illustrated in FIG. 2, a neurostimulation device that is implanted by the robotic tool and/or the implantation of the neurostimulation device may also be guided by the robotic navigation system. A lead stimulation device, e.g., a pulse generator, may be implanted by the robotic arm or via guidance of the robotic arm within therapeutic proximity of the target nerve. In one embodiment, the target nerve is the dorsal root ganglia, though other target nerves are within the scope of the present invention.

The robotic arm 116 may comprise a robotic element in the form of a cannula and/or a lead implant guide for placing the lead at the target nerve in the orientation and space prescribed during the pre-operative plan. In one embodiment the planning step includes determining the angle of the placement relative to the target nerve for optimal surgical results and or for simplicity of surgical procedure in implanting the lead of the neural stimulation device and/or the entire neural stimulation device via the robotic navigation system or based upon guidance therefrom.

In another embodiment of the invention the robotic arm 116 may comprise an effector end E that is a surgical element that functions as a retraction tool. In addition to making an incision, described above, the robotic arm 116 effector end E may include a robotic retraction element that allows for the location, sizing and shaping of the incision for access to the patient anatomy of interests. In one embodiment the anatomy of interest is a boney structure, or a portion thereof, in addition to the target nerve 110 of interest, or a portion thereof. In one embodiment the target nerve is the dorsal root ganglia. The retraction element, when present, allows for direct physical access to the target nerve 110 and/or direct visual access to the target nerve 110 and/or visualization of the lead with respect to the target nerve 110 on the display 106. In any of the above described methods for accessing and determining the location of the target nerve, the display shows the relative position of the robotic arm 116 and robotic tool or element at effector end E and its relative position to the target nerve 110.

Figure 3:
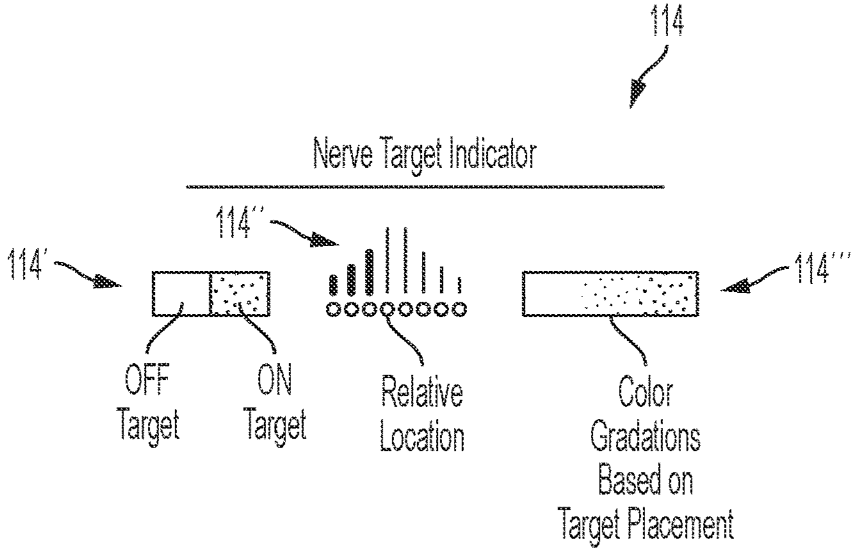
FIG. 3 illustrates three embodiments of one aspect of the present invention.

Yet another embodiment of the present invention is a visual indicator of the surgical lead position with respect to the target nerve, as shown in FIGS. 2-4 and that may comprise one or more lights. The display 106 may comprise visual indicator 114, or visual indicator 114 may be provided separately. As described above, the position of the robotic arm 116 with respect to the patient's anatomy can be visualized and displayed on the display 106, as can the surgical elements being deployed by the effector end E of the robotic arm 116, as can the elements of the neuromodulation device, including the implantable pulse generator and the leads. More specifically, the leads of the present invention include a distal portion for placement over the target nerve, such distal portion including one or more electrodes for contact with the target nerve 110 or near the target nerve 110, i.e., within therapeutic proximity of the target nerve 110, in order to provide a neural stimulation energy to the target nerve 110. The lead may further include a radiopaque marker for additional enhanced visibility of the lead to the camera and more accurate visualization of the lead on the display 106.

Various embodiments of a visual indicator of lead placement relative to the target nerve are described here with reference to the present invention. Three exemplary embodiments of a visual indicator is provided in FIG. 3 and may comprise the use of a light annunciator and/or different colors when viewed on the display for the elements identified as the target nerve location and a separate color for the elements identified as the lead location, in order to allow for visual differentiation of the two elements during the procedure. Additionally, optimal placement indicators may be provided by the display such as visual or aural or even tactile feedback element when the distal portion of the lead is optimally placed over the target nerve, in accordance with the pre-operative plan.

In one embodiment, visual indicator 114' may comprise one or more lights that indicate whether the lead placement location is within a predetermined location range or outside of the predetermined location range. In this embodiment, if within the predetermined range, the visual indicator 114' may be lit. In a related embodiment, if outside the predetermined range, another visual indicator light may be lit. Relatedly, another embodiment of visual indicator 114' may comprise the color of the indicator light as indicated on the display, when being placed over the nerve target, may change from a first color to a second color as the lead is placed or advanced from a non-optimal position (first color) to an optimal position (second color), in some embodiments the first color may be actuate when the lead is advanced within a predetermined location range, but not at an optimized location, while the second color may indicate optimized lead location. As such, this provides an affirmative indicator when the optimal placement has been achieved. In another embodiment, gradations of color may be used as the lead more closely approaches the optimal placement over the nerve target. Additionally or separately, an aural indicator of optimal lead placement may be provided as well via a speaker from the display device or control system.

In yet another embodiment shown in FIG. 3, the visual indicator 114" may comprise a graphical display that may be used to indicate the placement of the lead with respect to the nerve target having low bars when placed in an area not optimal or near optimal relative location and a higher bar or set of bars when placed in a more optimal relative location. Likewise lower bars can have different colors depending on where the lead is placed relative to the optimal positioning with different gradations of color based upon the relative position of the lead over the target nerve. A bar graph 114" embodiment, or a line graph comprising a series of at least two lights 114'" may be employed to display the location of the lead as it is being placed by the robotic arm 116 and in some cases relative to the location of the target nerve.

It shall be appreciated that the positioning of the lead and/or neurostimulation device with respect to the target nerve may be utilized to guide not only placement of the electrode with respect to the target nerve but also the angle of approach and entry and exit of the portions of the lead not necessarily in direct contact with the target nerve.

FIG. 4 provides an exemplary image displayed on the display 106 wherein a lead with accompanying electrode(s) is positioned with a prescribed lead orientation which may be provided for by execution of the programmed instructions of control system 102 that result in actuation of the robotic arm and positioning and/or orienting the lead within therapeutic proximity of a target nerve. In addition to the visual image displayed, a visual indicator, e.g., 114 may be provided on display 106 to provide additional information to the operator.

The present invention may further comprise a safety control system for controlling the robotic arm during spinal procedure and that may be embodied within, and executed by the programmed instructions of the processor P of the control system 102. In one embodiment the control system 102 and/or robotic arm may require an affirmative confirmation from a surgeon prior to making an incision or performing surgical step of the procedure, including any of the steps of the surgical procedure described above and/or to be described below.

In yet another embodiment of the present invention, the safety control system may require separate affirmative confirmation steps prior to the surgical step being performed by the robotic arm 116. By way of example, the incision location and angle of entry may require separate confirmations via an actuation step performed by the surgeon in order to enable the performance of the incision, or other, surgical step,that may require actuating actuator shown in FIG. 2.

The safety control system further includes safety control aspects to ensure patient safety and successful surgical procedures. In one embodiment, a surgical step is occurring at a predetermined rate of penetration, as programmed into the safety control system, that allows for monitoring of the surgical step comprising advancing a lead and/or implantable pulse generator disposed on or engaged with the effector end E of robotic arm 116 with minimal risk of injury to the patient and/or minimal risk of diverging from the surgical plan beyond a predetermined margin. In another embodiment, the rate of advancement of the surgical instrument and/or effector end E of robotic arm 116 with tool attached or engaged thereto, e.g., lead or a lead delivery guide tool as shown in FIG. 6 may be predetermined by the safety control system to have either a constant rate of advancement or a variable rate of advancement that slows down as it advances toward a predetermined location, as determined by the requirements and/or risks and/or degree of control required by a particular surgical step and/or surgical operation.

The safety control system may further include an element for interrupting the surgical step. In one embodiment, the safety control system includes a surgical interrupt element that is accessible to the surgeon. When the surgical step interruption element is actuated, the safety control system causes the surgical elements currently in use to case operation. In one embodiment, the safety control system may cause the surgical element be retracted a predetermined distance from its current position upon actuation of the interruption element. In another embodiment, interruption of the surgical step results in the surgical element being maintained in its current position relative to the anatomical target but ceases to advance and/or mechanical movement and/or operation.

The monitoring of the surgical procedure by the surgeon can be done visually by viewing the patient's anatomy and robotic arm and surgical elements attached thereto. Alternatively or additionally, the surgical procedure can be monitored and assessed via the display which displays the position of the surgical element utilized by the robotic arm with respect to the patient's anatomy. The actuation of the safety control system is accessible by the surgeon in either mode of surgical procedure monitoring and performance.

Figure 5:
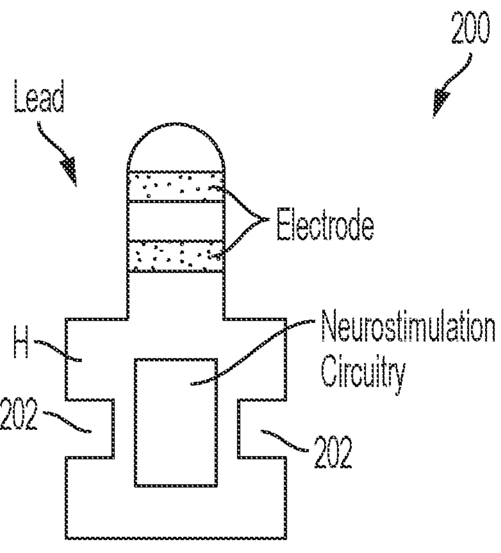
FIG. 5 illustrates a side view of one embodiment of the present invention.
Figure 6:
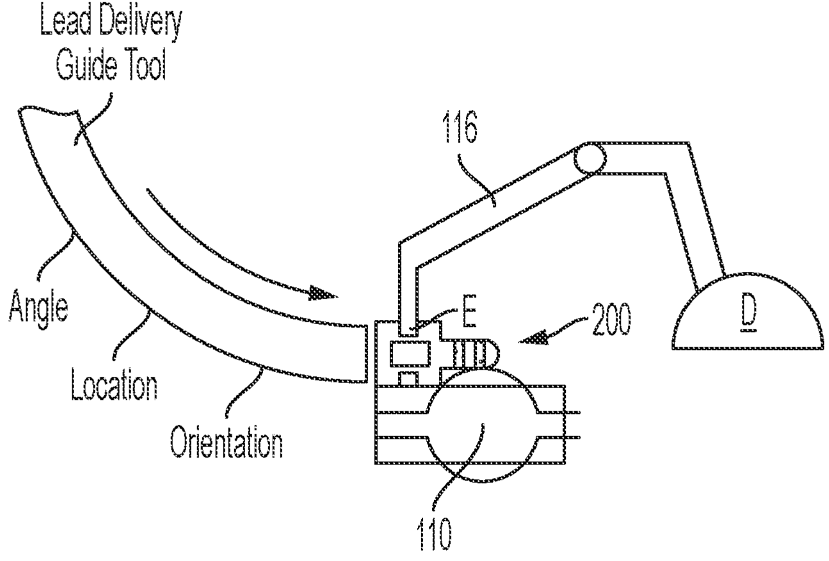
FIG. 6 illustrates a side, cutaway view of one embodiment of the present invention.

As shown in FIGS. 5 and 6, the present invention further includes a neuromodulation device 200 for implantation by a robotic surgical system 100. The neuromodulation device includes a unitary structure or housing H defining and/or containing a neurostimulation circuitry configured for generating electrical pulses and delivering the generated pulses to at least one electrode, but may by way of example have two, four, eight, sixteen or more electrodes, for delivering the electrical stimulation signal from the neurostimulation circuitry to the target nerve via the one or more electrodes when placed in therapeutic proximity to the target nerve 110.

The neuromodulation device 200 has one or more recesses 202 that enables engagement of the neuromodulation device 200 by the effector end E of robotic arm 116 during a surgical procedure. The recess(es) 202 allows the robotic arm 116 to grip the device 200 and to navigate the neuromodulation device 200 to the desired surgical location and at the prescribed surgical angle of approach and entry position. The device 200 further enables placement of the neural stimulation device at a target nerve by the robotic arm during a procedure.

As shown in FIG. 6, the neuromodulation device 200 may be placed on or within therapeutic proximity of the target nerve 110 using the robotic navigation system 100 described herein and the system 100 may comprise a lead delivery guide tool that may be adjusted or adjustable in the angle of entry, the location and orientation of the device 200. More specifically, the one or more electrodes of device 200 may be placed on or within therapeutic proximity of the target nerve using the robotic navigation system 100 described herein.

Various embodiments of the neuromodulation device 200 allow for the neuromodulation device to be delivered by a cannula or via a lead placement guide that cooperates with the robotic arm directly. The neuromodulation device 200 may further include anchoring elements such as tines or equivalent structures. The neuromodulation device 200 may further include fiducial markers for visualization of the placement of the neuromodulation device over the target nerve on the display, wherein the fiducial markers are visible via the image or navigation camera system enabling the display of the orientation and placement of the neural stimulation device in the patient's anatomy relative to the target nerve.

In certain embodiments of the robotic navigation system 100, a retraction element may be disposed at the effector end E of robotic arm 116 and may be used to enable direct visual and/or physical access to the target nerve and/or visualization of the neuromodulation device relative to the target nerve via the display, such as through the use of a fiber optic camera in the deliver cannula. Any of the above visualization or access approaches allow for guided navigation under the control of a surgeon or guided navigation performed by the robot under the supervision of the surgeon in accordance with embodiments of safety control parameters described above for the placement of the neuromodulation device over a target nerve.

The neuromodulation device embodiment 200 may be such that it is externally powered by an RF antennae housed within the neuromodulation device 200 that is powered by an external power source for activation. Alternatively, the neuromodulation device 200 may have an internal battery for power generation. Due to the small form factor the plug of tissue used to access the patient's anatomy may provide for the anchoring of the implanted neuromodulation device and minimize potential migration of the neuromodulation device. It is further understood that multiple neuromodulation device devices as described herein may be implanted at multiple dorsal root ganglia around the surgical region of interest each being separately powered or, alternatively, jointly connected to a power source or each powered by an external power source.

The various embodiments of the present invention described above may be used alone or in combination with each other in accordance with the scope and spirit of the present invention.

The invention claimed is:

1. A robotic navigation system for identifying a target nerve within a surgical site for implanting a neuromodulation device comprising at one or more leads within the surgical site, comprising:

a robotic arm, the robotic arm comprising an effector end, at least one recess defined by the neuromodulation device configured to allow the effector end to grip the neuromodulation device at the at least one recess;

a control system configured to receive three-dimensional preoperative data comprising a spatial location of bone structures of two adjacent vertebrae within the surgical site, the control system comprising a registration system configured to register a coordinate system of the robotic arm with the received three-dimensional preoperative data, wherein the robotic arm is in operative connection and communication with the control system;

a display screen in operative connection and communication with the control system and configured to display the spatial location of the bone structures; wherein the control system is configured to calculate an estimated target nerve location based upon the three-dimensional preoperative data, wherein the control system is configured to display a virtual indicator of the calculated target nerve location on the display screen in the estimated target nerve location relative to the spatial location of the bone structures;

a visual indicator comprising at least one light annunciator configured for light-annunciated guidance of placement and position of each one of the one or more leads relative to the target nerve, wherein the at least one light annunciator comprises a color-coded annunciator comprising: a first color annunciating a position of each one of the one or more leads that is within a predetermined range of optimal placement and position relative to the target nerve, and a second color annunciating a position of each one of the one or more leads that is outside the predetermined range of optimal placement, wherein the visual indicator is in operative communication and connection with the robotic arm and the display screen;

a safety control system in operative connection and communication with the control system and configured to be controlled by the control system, wherein the safety control system and/or the control system is configured to control the robotic arm, wherein the robotic arm is configured to receive instructions from the control system based on a preoperative plan based on the three-dimensional preoperative data and the calculated estimated target nerve location, wherein the control system is configured to position the robotic arm preoperatively according to the received instructions over a predetermined incision location with a predetermined angle of entry and a predetermined depth, wherein the effector end of the robotic arm comprises an incision tool configured to make an incision at the predetermined incision location at the predetermined angle of entry and the predetermined incision depth according to the received instructions from the control system, wherein the safety control system requires instructions requiring separate affirmative preoperative confirmation steps from a surgeon to confirm the preoperative position of the robotic arm prior to making the incision, the separate affirmative preoperative confirmation steps including (1) the preoperative position of the robotic arm regarding the predetermined location of the incision, (2) the predetermined angle of entry, and (3) the predetermined incision depth, and wherein each one of the separate preoperative confirmation steps require separate actuation steps performed by the surgeon.

2. The robotic navigation system in accordance with claim 1, wherein the target nerve is a dorsal root ganglion.

3. The robotic navigation system in accordance with claim 1, wherein the target nerve is a spinal cord.

4. The robotic navigation system of claim 1, wherein the estimated target nerve location is based upon an MRI.

5. The robotic navigation system of claim 1, wherein the calculated estimated target nerve location is based upon an estimated anatomical distance from the bone structures.

6. The robotic navigation system of claim 1, wherein the calculated estimated target nerve location is based upon fiducial markers registered by the registration system.

7. The robotic navigation system of claim 1, wherein the estimated target nerve location is using machine learning, said machine learning providing said estimated target nerve location based upon an annotated training set of multiple bone structure images and target nerve locations.

8. The robotic navigation system of claim 1, wherein the estimated target nerve location is based upon an evoked response.

* * * * *